US007004924B1

(12) United States Patent
Brugger et al.

(10) Patent No.: US 7,004,924 B1
(45) Date of Patent: Feb. 28, 2006

(54) METHODS, SYSTEMS, AND KITS FOR THE EXTRACORPOREAL PROCESSING OF BLOOD

(75) Inventors: James M. Brugger, Newburyport, MA (US); Charles David Finch, Clinton, MS (US); Jeffrey H. Burbank, Boxford, MA (US)

(73) Assignee: NxStage Medical, Inc., Lawrence, MA (US)

( * ) Notice: Subject to any disclaimer, the term of this patent is extended or adjusted under 35 U.S.C. 154(b) by 0 days.

(21) Appl. No.: 09/174,721

(22) Filed: Oct. 19, 1998

Related U.S. Application Data

(60) Provisional application No. 60/074,387, filed on Feb. 11, 1998.

(51) Int. Cl.
*A61M 1/03* (2006.01)
*A61M 37/00* (2006.01)
*A61M 5/00* (2006.01)
*A61N 1/362* (2006.01)

(52) U.S. Cl. ............... 604/6.13; 604/4.01; 604/65; 600/16

(58) Field of Classification Search ............. 604/4, 604/7, 5, 6, 48, 95, 118, 123, 151, 186, 246, 604/540, 543, 4.01–6.13, 65, 67, 28, 508; 600/16; 73/861.25, 19.1; 417/19–54
See application file for complete search history.

(56) References Cited

U.S. PATENT DOCUMENTS

| | | | | |
|---|---|---|---|---|
| 4,108,574 | A | * | 8/1978 | Bartley et al. ............ 417/19 |
| 4,112,713 | A | * | 9/1978 | Stasz et al. ............. 73/194 |
| 4,173,144 | A | * | 11/1979 | Pounder ................. 73/229 |
| 4,181,132 | A | | 1/1980 | Parks ................ 128/399 |
| 4,401,431 | A | | 8/1983 | Arp |
| 4,670,007 | A | * | 6/1987 | Wheeldon et al. ........ 604/65 |
| 4,690,002 | A | * | 9/1987 | Hubbard et al. ....... 73/861.25 |
| 4,784,643 | A | * | 11/1988 | Siretchi et al. ......... 604/122 |
| 4,828,543 | A | | 5/1989 | Weiss et al. |
| 4,902,276 | A | * | 2/1990 | Zakko ................. 604/28 |
| 5,391,142 | A | * | 2/1995 | Sites et al. ............ 604/6.13 |
| 5,533,957 | A | * | 7/1996 | Aldea ................. 600/16 |
| 5,562,617 | A | | 10/1996 | Finch, Jr. et al. ........ 604/93 |
| 5,618,441 | A | * | 4/1997 | Rosa et al. ............ 210/739 |
| 5,704,766 | A | * | 1/1998 | Fennel et al. ........... 417/42 |
| 5,814,004 | A | * | 9/1998 | Tamari .................. 604/4 |
| 5,879,361 | A | * | 3/1999 | Nash ................. 606/159 |
| 5,928,179 | A | * | 7/1999 | Plotkin ................. 604/4 |
| 6,135,943 | A | | 10/2000 | Yu et al. |
| 2001/0016699 | A1 | * | 8/2001 | Burbank et al. ........ 604/4.01 |

FOREIGN PATENT DOCUMENTS

| | | |
|---|---|---|
| DE | 37 20 667 A1 | 6/1987 |
| JP | 10103286 * | 4/1995 |
| WO | 03/103533 | 12/2003 |

* cited by examiner

*Primary Examiner*—Nicholas D. Lucchesi
*Assistant Examiner*—Roz Maiorino
(74) *Attorney, Agent, or Firm*—Proskauer Rose LLP

(57) ABSTRACT

Methods, systems, and kits for extracorporeally circulating and processing blood are described. The systems include a pump, a processing unit, and blood drawn return lines for accessing a patient's vasculature. Blood flow through the return line is measured and pump speed controlled to maintain a desired blood flow rate. Alarm conditions can be initiated when expected pump performance differs from that needed to maintain the control point flow rate. By using a ultrasonic flow detector, gas bubbles in the blood flow can be detected.

15 Claims, 2 Drawing Sheets

METHODS, SYSTEMS, AND KITS FOR THE EXTRACORPOREAL PROCESSING OF BLOOD

This application is a continuation-in-part of Provisional Application No. 60/074,387, filed on Feb. 11, 1998, the full disclosure of which is incorporated herein by reference.

BACKGROUND OF THE INVENTION

1. Field of the Invention

The present invention relates generally to medical methods, apparatus, and kits. More particularly, the present invention relates to methods, systems, and kits for pumping blood through extracorporeal processing units and returning the processed blood to patients.

A variety of extracorporeal blood therapies exist which require blood withdrawal, passage through processing equipment, and return of the processed blood to the patient. Examples of such extracorporeal blood therapies include hemodialysis, hemofiltration, hemodiafiltration, apheresis, and the like. Access to a patient's vasculature may be provided through implanted ports, transcutaneous catheters, direct needle access into blood vessels, and other approaches. Once blood withdrawal and blood return lines have been established, the blood is pumped through an appropriate processing unit, such as a dialysis unit, filtration unit, apheresis unit, or the like and the treated blood returned to the patient.

It is easy to appreciate that careful control and monitoring of the extracorporeal blood circulation is important to both successful blood treatment and patient safety. Important parameters and conditions to be monitored and controlled include blood flow rate, line pressures upstream and downstream of the pump, blockages in the blood draw line, blockages in the blood return line, air leakage into the recirculation blood stream, and the like. Previous extracorporeal blood circulation systems have often relied on setting the speed of a peristaltic pump to control the blood flow rate. Since peristaltic pumps operate by the positive displacement of blood, it has been assumed that the flow rate will be fixed by the pump speed.

As recognized by the inventors herein, however, that assumption is not warranted. Peristaltic pumps, also referred to tube or roller pumps, rely on moving rollers to progressively "pinch" a tube to advance a series of small blood volumes through the tube and out of the pump. So long as the inlet pressure to the pump tube is generally constant, the pump output will be a predictable function of pump speed. In the case of extracorporeal blood circulation, however, where blood is being drawn through a relatively small needle or other access tube, the inlet pressure of blood to the pump can vary significantly. Moreover, the flow characteristics of a peristaltic pump may vary over time so that the volumetric output will change even if the inlet pressure remains generally constant. While use of a peristaltic pump does have a number of advantages, e.g. there are much less likely to apply a deleterious negative pressure to the blood being circulated, calculating the flow rate based on pump speed alone is nonetheless problematic.

To help monitor whether the pump is starved of inlet blood flow (which can alter the flow rate as discussed above), some prior art systems have employed pressure monitors on the blood draw and/or return lines. A fall in pressure in the draw line indicates that a blockage or other failure has occurred in the draw line, that the access needle is too small and/or that the access vessel has undergone a partial or total collapse. In contrast, a rise in pressure in the return line indicates the occurrence of an occlusion or other problem in the return line and/or the occurrence of a blockage in the vessel, access device, or fistula. In order to help assure sterility, pressure measurement has usually been performed using drip chambers where the pressure is transmitted via an isolated air line and a transducer protector to the appropriate transducer. Such drip chambers, however, increase the cost of the catheters (blood lines) used for the draw and return lines and the air interface can cause clotting, air entrapment, and other flow problems in the blood recirculation.

For these reasons, it would be desirable to provide improved methods, systems, and kits for the extracorporeal recirculation and processing of blood. In particular, it would be desirable to provide extracorporeal blood flow systems having improved blood flow rate control as well as improved capability for monitoring proper operation of the blood circulation circuit. Such systems should permit monitoring with a reduced risk of contaminating the blood or causing clotting, air entrapment, or other degradation of the blood. Preferably, such improved systems and system components will permit relatively low cost operation, and specifically will permit implementation without the use of drip chambers as required by certain prior art systems. At least some of these objectives will be met by the invention described hereinafter.

2. Description of the Background Art

U.S. Pat. No. 5,562,617 assigned to the assignee of the present application, describes a system of implantable ports and catheters for accessing a patient's vasculature, which system could be used together with the extracorporeal blood recirculation systems of the present invention. U.S. Pat. No. 4,181,132, describing an extracorporeal processing and blood circulation unit which is attached to a patient's vasculature through an implanted port. Co-pending applications assigned to the assignee of the present invention and including related subject matter include. These patents and pending applications are incorporated herein by reference.

SUMMARY OF THE INVENTION

The present invention provides improved methods, systems, and kits for the extracorporeal circulation and processing of blood for a variety of purposes including but not limited to hemodialysis, hemofiltration, hemodifiltration, apheresis and the like. Particular improvements provided by the present invention include non-contact measurement of the actual blood flow rate in the circuit, preferably at a location close or adjacent to the return access site on the patient. Based on such actual blood flow measurement, the speed of the blood pump in the flow system can be adjusted to maintain the measured blood flow rate at a control point. Thus, operation of the of the system does not rely on an inferred flow rate based on the operational speed of the pump. Moreover, by monitoring the pump operation characteristics, system failures can be detected. For example, a measured blood flow rate which is significantly below an expected blood flow rate calculated from the speed at which the pump is being driven and known pump characteristics indicates a system failure, most likely loss of blood flow in the return line. Actual power consumption by the pump which is significantly above an expected power consumption based on the measured blood flow rate indicates a failure in the blood circulation system, most likely a blockage in the return line or elsewhere distal to the pump. The non-contact flow measurement is preferably performed using an ultrasonic flow detector. Output of the ultrasonic flow detector is also useful for indicating the presence of air in the blood flow which can result from a leak anywhere proximal to (upstream of) the flow detector. Air leaks may also be detected by an actual pump speed which is higher than expected for the measured blood rate. The methods and systems for implementing these safety and monitoring features are described in more detail below.

Methods according to the present invention for extracorporeally processing blood comprise pumping blood with a pump having a nominal relationship between pump speed and flow rate, i.e., pump output may be approximated based on pump speed but will be variable due to the factors discussed above. Such pumps will usually be positive displacement pumps, typically being peristaltic pumps which are often preferred since they permit complete isolation of the blood and reduced risk of blood contamination. It would be possible, however, to utilize centrifical and other non-positive displacement pumps so long as the pumps permit monitoring of the pump speed and prediction of an expected flow rate based on the pump speed.

The blood flow rate delivered by the pump is measured, and the pump speed is controlled to maintain the measured blood flow at a control point, typically in the range from 100 ml/min to 1000 ml/min, preferably from 250 ml/min to 500 ml/min. Pumped blood is processed in any desired manner, including dialysis, hemofiltration, hemodifiltration, apheresis, and the like, and then returned to the patient. Usually, the blood will be withdrawn from an artery and returned to a vein or will be withdrawn from a vein and returned to a vein. It is also possible, although generally less preferred, to both draw the blood from and return the blood to an artery.

The blood flow measuring step is preferably performed with a non-contact flow sensing device, such as an ultrasonic flow sensor. By "non-contact," it is meant that no component of the measuring device need be immersed in or otherwise in contact with the flowing blood. Preferably, the flow sensors will be mounted or attached over the blood return line or other conduit of the system. Suitable ultrasonic flow sensors are commercially available from suppliers, such as Transonics, Ithaca, N.Y. Other suitable non-contact flow sensing devices include magnetic flow meters, optical flow detectors, electrical conductance flow detectors, and the like. The ultrasonic or other non-contact flow measuring device is preferably mounted over an exterior surface of a blood return line to the patient, more preferably being close to the blood return site on the patient so that the blood is monitored immediately prior to its return to the patient. Use of the ultrasonic flow sensing device also permits the detection of entrained air or other gases in the blood since the ultrasonic signal generated by air passing through the sensor will be immediately detectable i.e. the air will disrupt reflectance of the ultrasound signal which can be readily detected.

In a preferred aspect of the methods of the present invention, a failure in the extracorporeal blood flow circuit will be detected by calculating or otherwise determining an expected blood flow rate value based on the pump speed. Usually, such a determination can be made by a microprocessor or other controller that is controlling operation of the system as described in more detail below. The expected blood flow rate value is compared with the measured blood flow rate value (i.e., the value measured by the blood flow measurement device), and a difference is determined. If the difference exceeds a threshold value, typically about 5% of the measured flow rate, usually about 10% of the measured flow rate, then an alarm condition will be initiated. An alarm condition may comprise an audible, visual, or other signal being initiated to alert the system user, and/or may include system shut down, or preferably both.

In a still further preferred aspect of the method of the present invention, the blood flow status through the system may be monitored by measuring or otherwise determining the actual power being consumed by the pump while it is operating to establish extracorporeal blood flow. An expected value of the power consumption level can be determined by the system based on the pump speed and measured blood flow rate. Any differences between the actual power level being consumed and the expected power level can then be determined. If such a difference exceeds a threshold value, typically above 5% of the measured power consumption, usually above 10% of the measured power consumption, then an alarm condition can be initiated. The alarm conditions may be any of those set forth above.

As a further safety measure, pressure of the blood flow in the return line from the processor to the patient may also be detected and monitored. Preferably, the pressure is monitored externally on the blood return line, e.g. by placing a radially inward constriction on the return flow line. Radially outward forces on the constriction can then be monitored and will increase as the pressure within the flow line increases. Such a system can be calibrated to provide a rough estimation of pressure within the blood return line and alarm conditions can be initiated when threshold values are exceeded.

Optionally, a safety valve can be placed externally on the blood return line to positively stop blood flow from the system should an alarm condition occur.

Systems according to the present invention comprise a pump, a processing unit, a blood draw line, a blood return line, an external flow detector which may be positioned over an exterior surface of the blood return line, and a control unit. The pump is of a type generally described above, preferably being a positive displacement pump, and more preferably being a peristaltic pump. The processing unit may be a convention hemodialysis, hemofiltration, hemodifiltration, or apheresis unit. The blood draw and return lines will typically comprise catheters which are connectable in the system. In particular, the blood draw line will be connectable between the patient and the pump, while the blood return line will be connectable between the processing unit and the patient. The control unit is preferably a microprocessor and is connectable to both the pump and the flow detector so that the control unit can monitor flow and control pump speed according to the methods described above.

In particular aspects of the system, the control unit will be programmed to perform other functions as described in connection with the methods above. In particular, the control unit can monitor the actual pump speed and actual blood flow rate to determine if the expected blood flow rate based on pump speed is being achieved. Further, the control unit can monitor power consumption by the pump to determine if it is higher or lower than the expected value of power consumption based on the measured blood flow rate. Still further, the control unit can monitor the output of an ultrasonic flow detector to determine if there are air or other gas bubbles entrained in the flowing blood. Still further, the control unit may be programmed to monitor pressure in the blood return line from an external pressure detector.

The present invention will still further comprise kits including system components together with instructions for use. In a specific embodiment, the kit may comprise a blood draw catheter, a blood return catheter, and instructions for use setting forth any of the methods described above. System components will typically be packaged in a conventional medical device package, such as a pouch, tray, box, tube, or the like. Instructions may be printed on a separate sheet of paper or may be printed in whole or in part on part of the package materials. Usually, the system components will be maintained in a sterile condition within the packaging.

In an additional aspect of the present invention, a method for extracorporeally processing blood comprises drawing blood from the patient and pumping the drawn blood with a peristaltic pump at a predetermined stroke volume and rate corresponding to a theoretical pumped blood flow rate, i.e. a theoretical or expected value of blood flow rate that can be calculated based upon the known stroke volume and actual rate at which the peristaltic pump is being driven. An actual blood flow rate delivered by the pump is directly measured using any of the techniques described above, and the measured actual blood flow rate is compared with the theoretical or calculated blood flow rate. In a first instance, an alarm condition is signaled if the difference between the actual blood flow rate and the theoretical blood flow rate exceeds a predetermined minimum or threshold value. In a second instance, the rate at which the peristaltic pump is being driven is altered or varied in order to change the pumped blood flow rate to a desired value, e.g. one that more closely matches the theoretical pumped flow rate. It will be appreciated, of course, that the theoretical blood flow rate will vary over time as the pump speed is varied so that the theoretical flow rate and a target or control point flow rate will not always be precisely the same. It will further be appreciated that both the alarm and control aspects of this method may be employed or together.

In yet another aspect of the present invention, apparatus for extracorporeally processing blood comprises tubing having connectors for drawing blood from a patient and returning blood to the patient, where the tubing is connected to or comprises a section of peristaltic pump tubing. A controller operates the peristaltic pump at a desired stroke volume and rate which, at least at the outset, corresponds to a theoretical pumped blood flow rate. Apparatus directly measures the actual blood flow rate delivered by the pump through the tubing, and further apparatus compares the measured actual blood flow rate with the theoretical pumped blood flow rate. A signal is generated corresponding to a difference between the theoretical and actual blood flow rates. A signal may be used to initiate an alarm condition and/or control the actual pump speed in order to return the actual blood flow rate to a desired level or control point. Preferably, all tubing in the apparatus will be free of air-containing chambers, such as drip chambers.

In a still further aspect of the present invention, a blood processing system comprises a pump operable at different speeds to convey blood through a path. The system further includes a sensor which monitors blood flow rate and optionally detects the presence of air in the blood flow. A controller is coupled to both the sensor and the pump in order to control pump speed (and thus blood flow rate) as a function of monitored flow rate. Usually, the controller adjusts the flow rate as a function of deviation between the monitored blood flow rate and a desired (set point) flow rate. The control algorithm can be proportional, integral, derivative, or virtually any other known control algorithm. Usually, the sensor will be an ultrasonic sensor as described above.

DESCRIPTION OF THE PREFERRED EMBODIMENT

Figure 1:
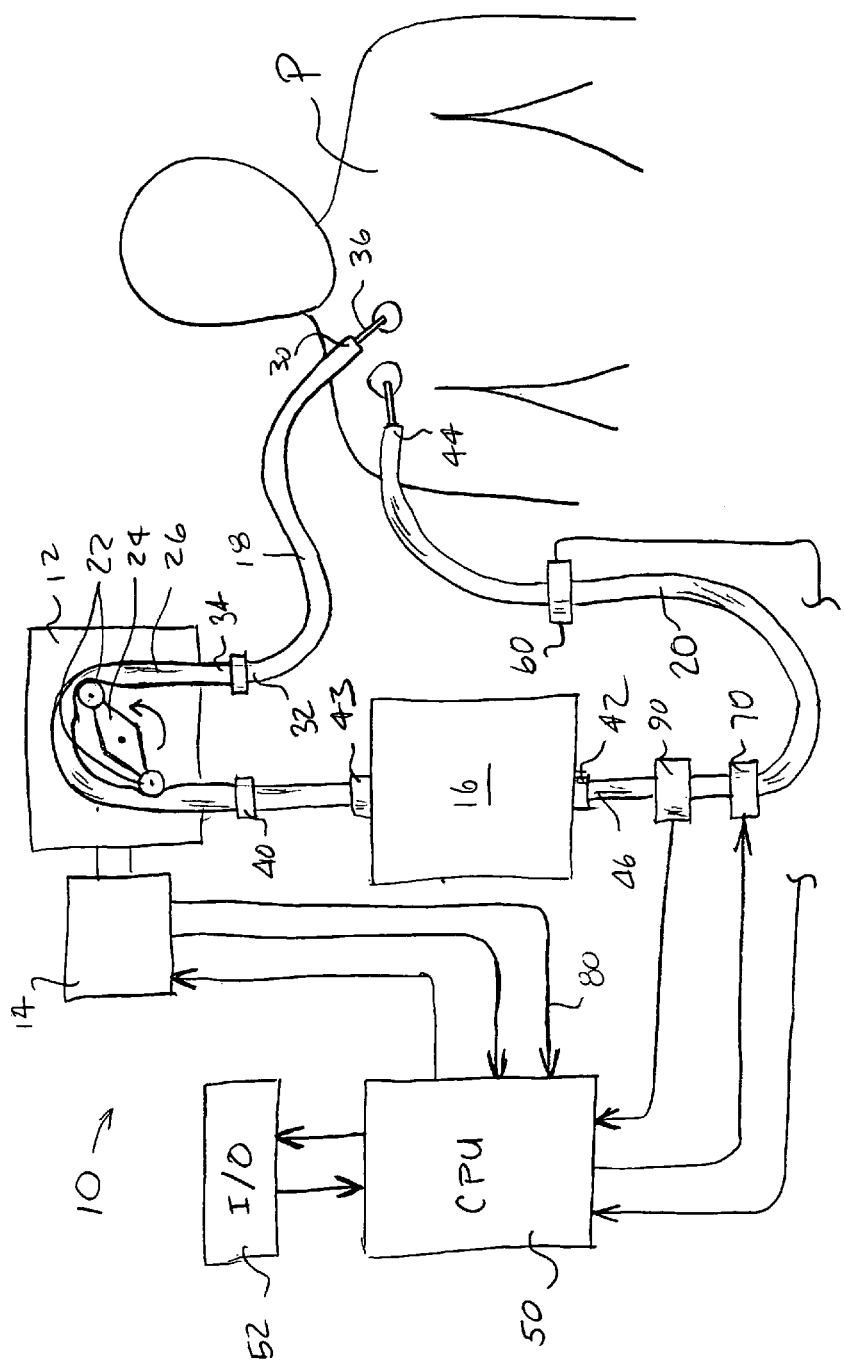
FIG. 1 is a schematic illustration of the system constructing in accordance with the principles of the present invention performing extracorporeal blood circulation and processing on a patient.
Figure 2:
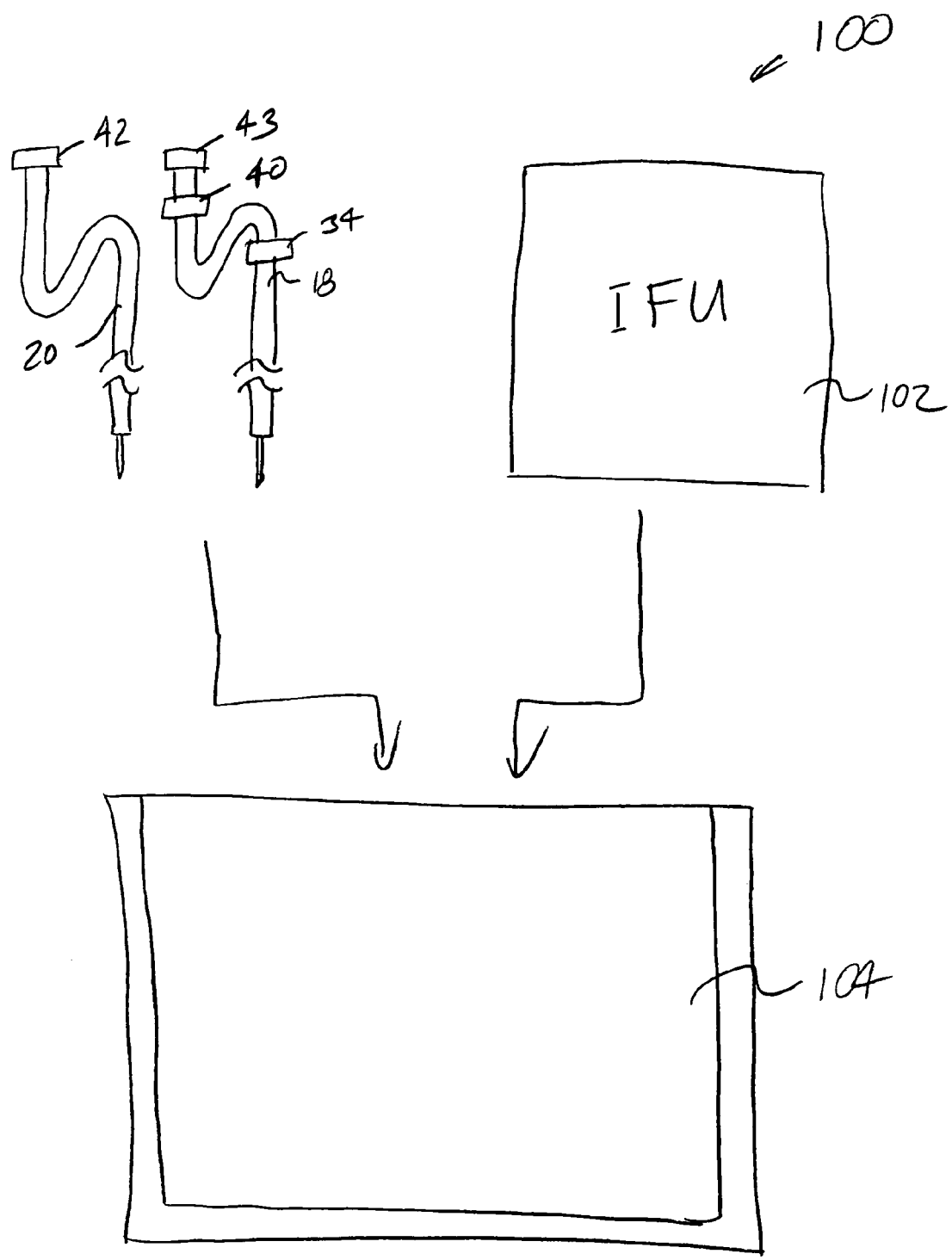
FIG. 2 illustrates an exemplary kit constructed in accordance with the principles of the present invention.

An exemplary system 10 for performing the methods of the present invention is illustrated in FIG. 1. The system 10 comprises a pump 12 coupled to a pump driver 14, a processing unit 16, a blood inlet line 18, and a blood return line 20. The pump 12 is illustrated as a peristaltic pump having a pair of opposed rollers 22 which are rotatably driven on an armature 24 to engage a resilient flow tube 26 (which may optionally be part of the replaceable inlet line 18). The driver 14 causes the armature 24 to rotate at a preselected rotational rate, typically comprising a digitally or servo controlled drive motor. The volumetric flow rate through the pump 12 may thus be approximated in the first instance by the internal diameter of the flow tube 26, stroke length of the pump (i.e., the length of tubing between the engagements points of the rollers 22), and the rotational rate of the armature 24. For the purposes of the present invention, it is important that there be a theoretical relationship between the pump speed, i.e. rotational rate of the armature 24, and the flow rate. In the case of the peristaltic pump, the theoretical relationship is linear. It will be appreciate that other types of pumps could also be utilized. Preferred pumps include other positive displacement pumps such as piston pumps, and the like, where the flow rate will have a linear relationship with the speed at which the pump is driven. It will also be possible to use centrifical pumps which have a non-linear, but predictable relationship between the pump speed and flow rate. The use of peristaltic pumps, however, is most preferred since in addition to providing a known, theoretically linear relationship between pump speed and flow, they also provide for complete isolation of the blood passing thorough the pump.

The processing unit 16 may be any device or apparatus intended for the extracorporeal treatment of blood. Most commonly, the processing unit 16 will be a hemodialysis unit, a hemofiltration, a hemodifiltration, a apheresis, or the like. Such processing units will typically have other associated components which are not shown in FIG. 1. For example, hemodialysis units will have the components necessary for continuously flowing a dialysate solution past an internal membrane to perform the desired dialysis function. Hemofiltration and diafiltration may have components for regenerating and controlling the filtering operation.

The blood draw line 18 will typically comprise a flexible tube or catheter having a distal end 30 adapted to access a patient's vasculature, e.g. a percutaneous access device adapted to connect to a subcutaneous port, and a proximal end 32 adapted to connect to an inlet port 34 of the pump 12. The distal end 30 can be adapted in a variety of ways. As illustrated, an access needle 36 is provided for percutaneous access to an implanted port, as generally described in a co-pending application Ser. No. 08/942,990, filed on Oct. 2, 1997, assigned to the assignee of the present application, the full disclosure of which is incorporated herein by reference. The access port will be subcutaneously connected to an artery or a vein to provide a source of blood for processing as more completely described in the co-pending application. The blood draw line could also be configured for connection to transcutaneous catheters, other implanted ports, or other blood access systems as described in the medical and patent literature. For use in the present invention, tubes or catheters comprising the blood draw line will typically have inner lumen diameters in the range from 2 mm to 8 mm, preferably from 4 mm to 6 mm, and lengths in the range from 50 cm to 300 cm, typically from 120 cm to 180 cm. The tubes or catheters may be composed of conventional materials, such as polyvinylchloride, silicone elastomer, polyurethane, and the like.

The processing unit 16 will receive blood from an outlet port 40 of the pump 12 via a connector 43. After passing through the processing unit 16 (typically a dialysis membrane or hemofiltration filter), the blood will flow outwardly through the port 42 and into the blood return line 20. The blood return line 20 usually comprises a tube or catheter having a distal end 44 adapted for accessing the patient vasculature typically through an implanted port or other conventional access device as described above. The proximal end 46 of the tube or catheter is preferably connectable directly to the outlet 42 of the processing unit 16. Thus, the extracorporeal circuit which is established comprises the blood draw line 18, the flow tube 26 of the pump 12, the processing unit 16, and the return line 20. Preferably, at least the draw line 18, flow tube 26, and return line 20 will be disposable and replaceable with new, sterile components to lower the risk of patient infection. Usually, at least the internal components of the processing unit 16 will also be disposable and replaceable for the same reason. In this way, all system components which contact the circulating blood will be initially sterile and used only once.

As described thus far, the extracorporeal circuit is generally conventional. One significant difference, however, with many previous systems is that neither the blood draw line nor the blood return line 20 need include drip chamber(s) to facilitate pressure monitoring (although the present invention does not preclude the use of drip chambers). It is a particular advantage of the present system that the use of such drip chambers is not necessary.

The system 10 is monitored and controlled by a control unit 50 which is typically a microprocessor based programmable controller integrated with the processing unit 16 but which may also be a separate personal computer or work station. The control unit 50 will have appropriate input/ output devices 52, such as knobs, dials, a display screen, keyboard, hardisk, floppy disk, CD drive, and the like, for permitting control, monitoring, and data acquisition in a generally conventional manner.

In particular, the control unit 50 will be connected to the pump driver 14 in order to permit the user to set the desired blood flow rate, typically in the ranges set forth above. The user will usually input a value of flow rate, typically in ml/min, and the control unit 50 will determine the corresponding pump speed which is expected to provide such a full rate based on the known pump characteristics. This selected flow rate will be the "expected" flow rate which is considered in a number of contexts below in connection with operation of the system. This user-selected "expected" flow rate will typically be a fixed value throughout the entire treatment protocol. The flow rate, however, could also be varied over time in which case the "expected" value for the flow rate will also vary as the treatment protocol progresses.

The actual blood flow rate is measured by a flow sensor 60 which is positioned to measure the output of the pump 12 after it passes through the processing unit 16. The sensor 60 is preferably a "non-contact" sensor which can be placed over an exterior surface of the blood return line 20 to measure the blood flow without any contact between the sensor and the blood itself. In this way, the flow sensor 60 can be reused without contamination from any individual patient. Preferably, the flow sensor 60 will be an ultrasonic flow sensor, such as model HT109, available from Transonics, Ithaca, N.Y. The ultrasonic sensor is particularly preferred, however, since it also permits monitoring of gas bubbles within the return line 20, as described in more detail below. Output of the flow sensor 60 is directed back to the control unit 50 where it is used for several purposes.

In particular, real-time determination of the blood flow rate through the return line 20 can be used for feedback control of the blood flow rate. While the blood flow rate may be nominally selected based on the pump speed, feedback of the actual flow from flow sensor 60 to the control unit 50 permits the control unit to adjust the pump speed to more precisely achieve the actual blood flow rate. The control unit 50 can be programmed to implement a variety of suitable control algorithms, including proportional control, derivative control, integral control, and combinations thereof.

In addition to real-time control of the blood flow rate, monitoring of the actual blood flow rate with flow sensor 60 permits the system 10 to monitoring for malfunctions. In the first instance, the control unit 50 can compare the actual flow rate as measured by the sensor 60 with the flow rate which would be expected for the pump 12 based on its known relationship between pump speed and flow output. If the pump speed is significantly higher than the speed which would be expected for achieving the actual flow rate, it is likely that the system is malfunctioning. For example, there may be a blockage between the patient and the pump 12 which starves the pump of blood. The pump 12 will then turn faster in response to the control algorithm which is attempting to maintain the flow control point.

Alternatively, there may be a leak between the output of the pump 12 and the flow detector 60, e.g. in the processing unit 16, which may also cause the pump to turn faster in an attempt to achieve the control point flow through the flow sensor. In either case, the control unit 50 can initiate an alarm condition when the pump speed is greater than the expected speed or the control point flow rate by some threshold amount, usually at least 1%, more usually at least 5%, and often 10%, or more, based on the preselect flow rate. The alarm condition may comprise shutting down the pump 12, initiating a visual or audible alarm and/or closing a safety valve 70 on the blood return line 20. Usually, all three actions will be taken.

When using an ultrasonic flow sensor 60, the system 10 can also detect the presence of air or other gas bubbles in the return line 20 to the patient. The ultrasonic reflective characteristics of blood and gas vary considerably, permitting the control unit 50 to detect the presence of the gas based on a very significant disruption in the detected ultrasonic signal. The presence of air or other gases in the blood return in the patient can result from a leak in the system anywhere upstream of the flow sensor 60. Regardless of the cause, the system 10 will initiate an alarm condition generally as described above in the case of pump overspeed. Since the controller 50 will know the cause, the alarm condition can indicate that it results from the presence of gas bubbles in the blood return line.

Knowledge of the actual flow rate provided by flow sensor 60 to the control unit 50 can also be used to detect a blockage in the downstream of the pump 12, usually in the return line 20. Any blockage downstream or distal from the pump 12 discharge port 40 will cause a greater pressure drop across the pump in order to maintain a given flow rate. Thus, by monitoring the power or current being consumed by the pump driver 14 through signal line 80, the actual power needed to drive the pump 12 can be compared with the expected power based on the actual flow rate. When the actual power consumed by the pump 12 exceeds the expected value by a threshold amount, typically at least 1%, usually at least 5%, and often 10% or more, based on the expected power consumption, then an alarm condition can be initiated generally as described above. An alarm condition can particularly indicated that there is a blockage in that portion of the system which is downstream or proximal from the pump 12.

Optionally, an external pressure sensor 90 can also be provided on the blood return line 20. The pressure sensor 90 can be a collar or other restriction which applies a small radially inward force on the resilient body of the return line 20. As blood flows through the return line, the corresponding radially outward pressure will be applied against the collar or other constriction. By monitoring this radially outward force, excess pressures through the return line 20 can be detected. Such secondary pressure monitoring is desirable for detecting significant overpressures, typically above 400 mmHg, and can be used to immediately shut down the system and initiate an alarm condition as described above.

In operation, the vasculature of a patient P is accessed by connecting the blood draw line 18 to an arterial or venous source within the patient. The blood draw line is then connected to the inlet port 34 of the pump 12. The blood return line 20 is then connected to a venous return location within the patient P and, at its other end, to an output port 42 of the processing unit 16. The flow sensor 60 will then be connected typically about the exterior of the blood return line 20. Optionally, the stop valve 70 and the overpressure detector 90 will also be connected to the exterior of the blood return line 20. The operation in the pump 12 will then be initiated to begin blood circulation through the draw line 18, pump 12, processing unit 16, and back to the patient to the return line 20. The blood flow rate will be controlled using the active control scheme described above, while system operation and malfunction will be monitored, also as described above.

The present invention will also provide kits 100 including some or all of the disposable components which can be used with the system 10 for performing the methods of the present invention. For example, the kit 100 can include tubes or catheters comprising the draw line 18 and return line 20 as well as instructions for use 102 setting forth methods for extracorporeally circulating blood as described above. The catheters 18 and 20 and instructions for use 102 will typically be sterilely packaged within a conventional medical device package 104, such as a pouch, tray, tube, box, or the line. Instructions for use 102 will usually be printed on a separate sheet of paper, but may also be printed in whole or in part on a portion of the packing materials.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A system for processing blood, said system comprising:
   a pump having a known relationship between pump speed and output flow rate;
   a processing unit connectable to receive blood from the pump;
   a blood draw line connectable between a patient and the pump;
   a blood return line connectable between the processing unit and the patient;
   an external flow detector that can be positioned adjacent to an exterior surface of the blood return line to provide a measured blood flow rate; and
   a control unit connectable to the pump and the external flow detector, wherein the control unit adjusts the pump speed to maintain the measured flow rate at a control point;
   wherein the control unit determines an expected blood flow rate based on the adjusted pump speed, determines a difference between the expected flow rate and the measured flow rate, and initiates an alarm condition when the difference exceeds a threshold value.

2. A system as in claim 1, wherein the pump is a positive displacement pump.

3. A system as in claim 2, wherein the positive displacement pump is a peristaltic pump.

4. A system as in claim 1, wherein the processing unit is selected from the group consisting of hemodialysis units, hemofiltration units, hemodiafiltration units, and apheresis units.

5. A system as in claim 1, wherein the blood draw line comprises a catheter having a patient access connector at one end and a pump connector at the other end, and wherein the return line comprises a catheter having a patient access connector at one end and a processing unit connector at the other end.

6. A system as in claim 5, wherein both catheters are free from drip chambers.

7. A system for processing blood, comprising:
   a fluid circuit connectable for drawing blood from patient;
   a pump connectable to said fluid circuit to pump drawn blood at a predetermined stroke volume and rate which corresponds to a theoretical pumped blood flow rate;
   a flow sensor connectable to said fluid circuit to directly measure the actual blood flow rate delivered by the pump;
   a controller configured to compare the actual blood flow rate with the rate of the pump, and;
   said controller being configured such that if a difference between said actual blood flow rate and a flow rate corresponding said rate of said pump exceeds a predetermined minimum value, generating an indication thereof.

8. The system of claim 7, wherein said controller is connected to control said pump and is configured to slow or stop said pump has said predetermined minimum value.

9. A system as in claim 7, wherein said flow sensor is a non-contact flow sensor.

10. A device for extracorporeally processing blood, comprising:
    a fluid circuit connectable for drawing blood from patient;
    a pump connectable to said fluid circuit to pump drawn blood at a predetermined stroke volume and rate which corresponds to a theoretical pumped blood flow rate;
    a flow sensor connectable to said fluid circuit to directly measure the actual blood flow rate delivered by the pump;
    a controller configured to compare the actual blood flow rate with a rate corresponding to the pump speed, and;
    said controller being configured such that if a difference of a predetermined minimum value exists between said actual blood flow rate and the rate corresponding to the pump speed, actual blood flow rate and the rate corresponding to the pump speed" rather than altering the pumping speed so the blood flow rate corresponding to the pump speed has a value that more closely matches the actual blood flow rate.

11. Apparatus for extracorporeally processing blood, comprising:
an extracorporeal blood treatment device including a positive displacement pump with a controller and configured to pump blood at a rate selected by said controller;
a flow sensor configured to measure an actual blood flow rate of the pump;
said controller being configured to determine whether a high pressure condition exists from a flow rate indicated by said flow sensor and a flow rate indicated by said pump speed and to generate a signal in response thereto indicating whether a theoretical flow rate based on said pump speed corresponds to the flow rate indicated by said flow sensor;
said signal indicating a command to change a speed of said pump such that said theoretical and measured flow rates are closer in magnitude.

12. Apparatus for extracorporeally processing blood, comprising:
a blood circuit with a blood flow sensor and a pump;
a controller configured to control a speed of said pump to maintain a blood flow in said blood circuit, indicated by said blood flow sensor, at a control point;
a processing mechanism to process blood in said blood circuit;
said controller being configured to detect and generate an indication of a failure in the extracorporeal blood flood flow circuit responsively to a comparison of said pump speed and the measured blood flow rate value such that said indication is generated when a theoretical flow rate of said pump is different by a threshold amount from the measure flow rate value.

13. Apparatus as in claim 12 further comprising an alarm configured to activate in response to said indication.

14. Apparatus as in claim 12 wherein said processing mechanism is configured to perform one of dialysis, hemofiltration, hemodifiltration, and apheresis.

15. Apparatus as in claim 12 wherein said controller calculates a theoretical flow rate from said pump speed, compares a result to the measured blood flow rate, compares a difference thereof to a threshold value, and generates an error signal responsively to said difference thereof.

* * * * *